United States Patent [19]

Vecchi

[11] Patent Number: 5,578,734
[45] Date of Patent: Nov. 26, 1996

[54] METHOD FOR THE PREPARATION OF S-(+)-ETHODOLIC ACID AND SALINE DERIVATIVES

[75] Inventor: Giuseppe Vecchi, Aldesago, Switzerland

[73] Assignee: APR Applied Pharma Research SA, Stabio, Switzerland

[21] Appl. No.: 266,795

[22] Filed: Jun. 29, 1994

[51] Int. Cl.$^6$ .............................................. C07D 491/052
[52] U.S. Cl. .............................................................. 548/432
[58] Field of Search ............................................. 548/432

[56] References Cited

U.S. PATENT DOCUMENTS

| | | | |
|---|---|---|---|
| 4,501,899 | 2/1985 | Abraham et al. | 548/432 |
| 4,515,961 | 5/1985 | Demerson et al. | 548/432 |
| 4,520,203 | 5/1985 | Abraham et al. | 548/432 |
| 4,544,757 | 10/1985 | Demerson et al. | 548/432 |
| 4,886,886 | 12/1989 | McKittrick et al. | 548/432 |
| 5,447,946 | 9/1995 | Kurono et al. | 514/389 |

OTHER PUBLICATIONS

Humber, L. et al., J. Med. Chem., 1986, vol. 29, pp. 871–874.
Demerson, C. et al., J. Med. Chem. vol. 26, 1983, pp. 1778–1780.
Jacques, J. et al., Enantiomers, Racemates and Resolutions, John Wiley & Sons, New York, 1981, pp. 253–259.

*Primary Examiner*—Jacqueline Haley
*Attorney, Agent, or Firm*—Nixon & Vanderhye

[57] ABSTRACT

Method for optically resolving an enantiomeric mixture of ethodolic acid to produce the S (+) enantiomer is provided wherein the enantiomeric mixture is salified with at least 0.5 moles per mole of a mixture of alpha-(+)-phenethylamine enantiomers in an organic solvent. The resulting precipitate containing the salt of optically active phenethylamine and the S-(+)-enantiomer of the ethodolic acid is separated followed by isolation of the optically enantiomer. Salification of the acid with organic and inorganic bases, selected from basis amino acids, morpholine, aminopyridine and benzylalkyltrimethylammonium derivatives provides new therapeutically effective derivatives.

9 Claims, No Drawings

METHOD FOR THE PREPARATION OF S-(+)-ETHODOLIC ACID AND SALINE DERIVATIVES

The present invention refers to a method for preparing S-(+)-ethodolic acid by means of resolution of the corresponding racemic mixture. According to another embodiment, the invention covers the saline derivatives of the above mentioned active isomer.

BACKGROUND OF THE INVENTION

Ethodolic acid, chemically definable as 1,8-diethyl-1,3,4,9-tetrahydropyran [3,4-b]indole-1-acetic acid, has the following structural formula:

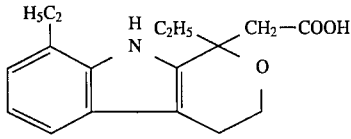

and is known and therapeutically used as an anti-inflammatory non steroidal active principle.

It has an asymmetrical centre and exists therefore as a mixture of two enantiomers. In the first report on the resolution of the two enantiomers (C. A. Demerson and al., J. Med. Chem., 26,1778, (1983)) the pharmacological activity is reported as almost totally due to the dextrorotatory isomer.

The absolute configuration of the (+) enantiomer has been subsequently determined and defined as S in accordance to the Cahn-Ingold-Prelog convention (C. A. Demerson, J. Med. Chem., 29,871,(1986)).

Various methodologies have been proposed in the course of years so as to carry out such resolution and, hence, the isolation of the pharmacologically active dextrorotatory isomer.

Canadian Patent No. 190230 to American Home Products Corp. discloses a resolution method which comprises the esterification of the racemic mixture of the two enantiomers with (−)-borneol and the further chromatographic separation in a silica column of the two diastereoisomers, from the hydrolysis of which the respective ethodolic acid enantiomers are obtained.

Regarding more specifically the dextrorotatory S isomer to be obtained, U.S. Pat. No. 4,501,899 entails the use of cholesterilaniline for the optical resolution.

In U.S. Pat. No. 4,515,961 the enrichment of an enantiomer by selective precipitation is described, triggered by the presence of an excess of enantiomer added to the crystallization mixture.

U.S. Pat. No. 4,520,203 teaches the resolution being accomplished by cinconine, whereas U.S. Pat. No. 4,544,757 describes still the (−)-borneal as the esterification agent.

The methods known until now show various drawbacks especially so far the yields are concerned, thus bringing about industrial problems.

DESCRIPTION OF THE INVENTION

The main object of the present invention is to provide a simple and industrially advantageous method for the optical resolution of a mixture of enantiomers of ethodolic acid, in order to obtain S-(+)-ethodolic acid in high yields and purity and with a reduced industrial cost.

The above object is achieved through the method of the present invention, which is characterized in that the racemic enantiomeric mixture of ethodolic acid is salified with at least 0.5 moles per mole of an enantiomeric mixture of alpha-(+)-phenethylamine, the salification being carried out in an organic solvent, and separation of the precipitate consisting of the optically active phenethylamine salt with the S-(+) ethodolic acid enantiomer, followed by the release of the desired optically active enantiomer with the usual and known processes.

In the preferred embodiment of the process of the present invention the above mentioned salification phase is made with one mole of optically active phenethylamine per mole of mixture of starting enantiomers whilst, according to a variation, the salification agent involves 0.5 moles of alpha-(+)-phenethylamine and 0.5 moles of triethylamine.

The preferred salification solvent is acetone, and a recrystallization of the phenethylamine salt of the S-(+) enantiomer of ethodolic acid is carried out with the same solvent before the release step of the desired isomer from the salt thereof. From the following examples, the main advantages of the process of this invention can be appreciated and so summarized:

1) The S-(+)-ethodolic acid is obtained at an enantiomeric purity higher than 95%.
2) The optically active amine is recovered with yields over 90%.
3) The optically active amine is recovered only in the release phase of the desired S-(+) enantiomer and not also on the mother liquors from the residues enriched in R-(−) isomer with, therefore, less consumption of optically active amine and decreased loss during the recovery thereof.
4) Simple, economic and industrially advantageous performance of the resolution procedure of the enantiomer mixture.
5) Possibility of directly preparing the saline derivatives of the optically active desired isomer, both with inorganic cations (alkali metals), with formation of inorganic salts, and with organic bases, such as basic aminoacids, preferably lysine, arginine and ornithine, or morpholine, aminopyridine and the like, as well as with bases having antibacterial activity, as for example benzylalkyltrimethylammonium derivatives.

These saline derivatives are also within the scope of the present invention and allow in particular to combine the specific properties of the ethodolic acid with those of the other portion of molecule added in the salification, the function of which is often complementary in comparison to the antiinflammatory one, as for instance in the case of salts with benzylalkyltrimethylammonium derivatives, with which the antiinflammatory activity is completed by means of a specific antibacterial activity.

EXAMPLES

The following examples show in detail, without limiting purposes, the process of the present invention.

EXAMPLE 1-A

Preparation Of the S-(+)-ethodolic acid 100 g R,S ethodolic acid (0.348 mole) are dissolved in acetone 300 ml and treated with 42.1 g (0,348 mole) of alpha-(+)-phenethylamine. As soon as the exothermic development due to the salification has ceased, the solution is kept between −5° and 10° C. for 4 hrs, with occasional stirring. The precipitate is vacuum filtered carefully eliminating as much as possible the mother liquors.

The precipitate (about 155 g wet, equal to about 100 g dry) is not washed with additional solvent, but recrystallized from 250 ml of boiling acetone.

The solution is allowed to cool slowly at room temperature and then kept at 0° C. overnight. The precipitate is vacuum filtered, washed with a little cold acetone and suspended in 250 ml of water. The pH is adjusted to 10 with concentrated sodium hydroxide, followed by extraction with toluene (2×100 ml). The combined organic phases are set aside to recover the phenethylamine.

The aqueous phase is slowly acidified with concentrated hydrochloric acid up to pH 2. A heavy oil is separated, which can be separated from the aqueous phase as such or by addition of 10 ml of methylene chloride. This organic phase that does not need drying, is rapidly poured in 200 ml of hexane at 5°–10° C. under strong stirring. After few minutes a white, crystalline precipitate is produced and vacuum filtered, thereafter washed with some hexane and dried at 60° C. The yield is 32 g (64%). The optical, specific rotatory power is +24,9° (C=3, ethanole, lett. +25.2). The acetone containing mother liquors from the two crystallizations is vacuum dried, and the residual oil undergoes the same above described procedures for the release of the amine from the salt. The toluene phases are combined with the previous ones and vacuum dried. Phenethylamine (38–40 g), which can be utilized at least once as such, without needing to be distilled, is thus recovered.

EXAMPLE 1-B 100 g R,S ethodolic acid are treated with 21.05 g of alpha-(+)-phenethylamine and 17.3 g triethylamine in 250 ml acetone, allowing to crystallize overnight at −5° to −10° C. The precipitate is filtered recrystallized from 100 ml boiling acetone. 31 g of S-(+)-ethodolic acid are obtained after standing overnight at 0° C.

EXAMPLE 2

Preparation of the potassium salt of ethodolic acid.

48.5 g ethodolic acid (0.169 mole) are dissolved in a solution of 6.76 g (0.169 mole) KOH in 42 ml distilled water. 100 ml toluene are added and the azeotrope toluene-water is vacuum distilled. This procedure is repeated twice. The oil so obtained is dissolved in 200 ml hexane at 10° C. under stirring until complete crystallization is achieved. The precipitate being hygroscopic, is rapidly vacuum filtered, and dried at 60° C. up to constant weight. The yield is 48.5 g (93%). By using this procedure with the S-(+)-ethodolic acid, the S-(+) salt of a specific rotatory power of +44.3° (c=1, water), is secured.

Example 2 describes the preparation of the potassium salt, but it is understood that such a procedure can be applied in the same way, with the obviously necessary changes of reactants and quantities, to the preparation of the other saline derivatives envisaged by the present invention and heretofore indicated.

I claim:

1. Method for optically resolving an enantiomeric mixture of ethodolic acid to produce S-(+)-ethodolic acid, said method comprising the steps of:

salifying an enantiomeric racemic mixture of ethodolic acid with at least 0.5 moles per mole of a mixture of alpha-(+)-phenethylamine enantiomers, said salification being carried out in acetone, to produce a precipitate containing a salt of optically active phenethylamine and the S-(+)-enantiomer of ethodolic acid;

separating said precipitate; and isolating the desired S-(+) enantiomer of ethodolic acid.

2. Method according to claim 1, wherein said racemic mixture is treated with one mole of alpha-(+)-phenethylamine for each mole of racemic mixture.

3. Method according to claim 1, wherein said racemic mixture is treated with a mixture containing 0.5 moles of alpha-(+)-phenethylamine and 0.5 moles of triethylamine.

4. Method according to claim 1, wherein said optically active phenethylamine is recovered when said S-(+) enantiomer is isolated from said precipitate.

5. Method for the preparation of a saline derivative of S-(+)-ethodolic acid which is an alkali metal salt of S-(+)-ethodolic acid or a salt of S-(+)-ethodolic acid with an organic base selected from the group consisting of a basic amino acid, morpholine, aminopyridine and a benzylalkyltrimethylammonium compound, said method comprising the steps of:

(a) dissolving equimolar quantities of ethodolic acid and said organic base in aqueous solution;

(b) adding an organic solvent capable of forming an azeotrope with water to said aqueous solution;

(c) conducting a vacuum azeotropic distillation to form a distillation residue; and (d) crystallizing the desired saline derivative from said distillation residue.

6. Method according to claim 5, wherein said organic solvent is toluene.

7. Method according to claim 5, wherein steps (a) and (b) are repeated more than once.

8. Method according to claim 5, wherein said ethodolic acid is S-(+)-ethodolic acid and the saline derivative is defined in step (d) is the S-(+)-salt.

9. Method according to claim 5, where said basic amino acid is selected from the group consisting of lysine, arginine and ornithine.

* * * * *